United States Patent [19]

Shen et al.

[11] Patent Number: 5,637,562

[45] Date of Patent: Jun. 10, 1997

[54] AGLUCONE ISOFLAVONE ENRICHED VEGETABLE PROTEIN CONCENTRATE AND PROCESS FOR PRODUCING

[75] Inventors: Jerome L. Shen; Barbara A. Bryan, both of St. Louis, Mo.

[73] Assignee: Protein Technologies International, Inc., St. Louis, Mo.

[21] Appl. No.: 307,751

[22] PCT Filed: Sep. 21, 1994

[86] PCT No.: PCT/US94/10696

§ 371 Date: Apr. 12, 1996

§ 102(e) Date: Apr. 12, 1996

[87] PCT Pub. No.: WO95/10529

PCT Pub. Date: Apr. 20, 1995

Related U.S. Application Data

[63] Continuation-in-part of Ser. No. 135,194, Oct. 12, 1993, abandoned.

[51] Int. Cl.⁶ ............... A61K 31/335; A61K 38/02; C07K 1/30; C12P 17/06
[52] U.S. Cl. ............... 514/2; 435/125; 514/456; 530/370; 530/378; 530/412; 530/419; 549/403
[58] Field of Search ............... 514/2, 8, 455, 514/456; 435/68.1, 125; 530/343, 370, 377, 378, 407, 412, 414, 419, 420, 427; 549/403

[56] References Cited

U.S. PATENT DOCUMENTS

| 3,870,805 | 3/1975 | Hayes et al. | 426/148 |
| 4,064,277 | 12/1977 | Yokotsuka et al. | 426/331 |
| 4,259,358 | 3/1981 | Duthie | 426/46 |
| 4,889,921 | 12/1989 | Diosady et al. | 530/377 |
| 5,320,949 | 6/1994 | Shen | 435/68.1 |
| 5,352,384 | 10/1994 | Shen | 252/398 |

FOREIGN PATENT DOCUMENTS 258669 10/1989 Japan.

OTHER PUBLICATIONS

Matsuura et al. β–Glucosidases from Soybeans Hydrolyze Daidzin and Genistin, J. Food Science, 1993, vol. 58, No. 1, pp. 144–147.

*Primary Examiner*—Jeffrey E. Russel
*Attorney, Agent, or Firm*—Richard B. Taylor

[57] ABSTRACT

Aglucone isoflavone enriched protein concentrates and processes for producing and recovering are disclosed. The process comprises an isoelectric wash of a vegetable protein material to provide a protein concentrate, which is slurried and reacted with a sufficient amount of beta-glucosidase enzyme or esterase enzyme for a time period, temperature, and pH sufficient to convert at least a majority of the glucone isoflavones contained in the concentrate to aglucone isoflavones.

51 Claims, No Drawings

AGLUCONE ISOFLAVONE ENRICHED VEGETABLE PROTEIN CONCENTRATE AND PROCESS FOR PRODUCING

This is a continuation-in-part of U.S. patent application Ser. No. 08/135,194, filed Oct. 12, 1993, now abandoned.

FIELD OF THE INVENTION

The present invention relates to the production of an aglucone isoflavone enriched vegetable protein concentrate, by washing a vegetable protein material to produce a vegetable protein concentrate and treating with one or more beta-glucosidase enzymes under conditions such that a majority of the glucone isoflavones are convened to aglucone isoflavones which are retained in the enriched protein concentrate.

BACKGROUND OF THE INVENTION

Isoflavones occur in a variety of leguminous plants, including vegetable protein materials such as soybeans. These compounds include daidzin, 6"-OAc daidzin, 6"-OMal daidzin, daidzein, genistin, 6"-OAc genistin, 6"-OMal genistin, genistein, glycitin, 6"-OAc glycitin, 6"-OMal glycitin, glycitein, biochanin A, formononetin, and coumestrol. Typically these compounds are associated with the inherent, bitter flavor of soybeans, and in the production of commercial products, such as isolates and concentrates, the focus has been to remove these materials. For example, in a conventional process for the production of a soy protein isolate, in which soy flakes are extracted with an aqueous alkaline medium, much of the isoflavones are solubilized in the extract, and remains solubilized in the whey, which is usually discarded following acid precipitation of the protein to form an isolate. Residual isoflavones left in the acid precipitated protein isolate are usually removed by exhaustive washing of the isolate.

It has been recently recognized that the isoflavones contained in vegetable proteins such as soybeans may inhibit the growth of human cancer cells, such as breast cancer cells and prostate cancer cells as described in the following articles: "Genistein Inhibition of the Growth of Human Breast Cancer Cells, Independence from Estrogen Receptors and the Multi-Drug Resistance Gene" by Peterson and Barnes, *Biochemical and Biophysical Research, Communications*, Vol. 179, No. 1, pp. 661–667, Aug. 30, 1991; "Genistein and Biochanin A Inhibit the Growth of Human Prostate Cancer Cells but not Epidermal Growth Factor Receptor Tyrosine Auto-phosphorylation" by Peterson and Barnes, *The Prostate*, Vol. 22, pp. 335–345 (1993); and "Soybeans Inhibit Mammary Tumors in Models of Breast Cancer" by Barnes, et al. *Mutagens and Carcinogens in the Diet*, pp. 239–253 (1990).

Of the above isoflavones, several exist as glucosides, or as glucones, with a glucose molecule attached, at the seven position as illustrated in the formula below. Several of the glucones such as the 6"-OAc genistin, contain an acetate group attached to the six position of the glucose molecule itself. While all of the isoflavones, including the glucosides are of interest in medical evaluation, the specific isoflavones of most interest are the aglucones, wherein the glucose molecule is not attached. These isoflavones are not as water soluble as the glucones or glucosides. Specific isoflavones in this category are daidzein, genistein, and glycitein. These aglucones have the following general formula:

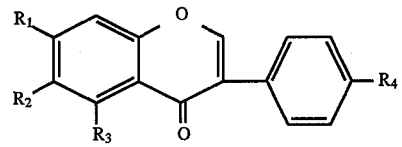

wherein, $R_1$, $R_2$, $R_3$ and $R_4$ may be selected from the group consisting of H, OH and $OCH_3$. It is therefore to the aglucones and enrichment of a vegetable protein concentrate with these materials to which the present invention is directed.

Methods are known in the art for converting glucone isoflavones to aglucone isoflavones, such as described in Japanese Patent Application 258,669 to Obata et al. Such processes achieve only a moderate extent of conversion and so are not desirable, particularly for large scale commercial operations. In addition, known processes such as described in the '669 application teach removing the isoflavones from the protein material and do not describe how to prepare an aglucone isoflavone enriched protein concentrate. Thus, there is a need for a process of converting at least a majority and preferably substantially all glucone isoflavones to aglucone isoflavones, and for producing an aglucone isoflavone enriched vegetable protein concentrate.

It is therefore an object of the present invention to provide an aglucone isoflavone enriched protein concentrate and a process for producing the same. This, and other objects, are specifically achieved in the detailed description of the present invention set forth below.

SUMMARY OF THE INVENTION

The present invention provides an aglucone isoflavone enriched vegetable protein concentrate and process for producing such. The methods for producing such comprise washing a vegetable protein material comprising glucone isoflavones with an aqueous solvent having a pH at about the isoelectric point of the protein material to produce a vegetable protein concentrate. The concentrate is then reacted with a sufficient amount of one or more beta-glucosidase enzymes for a time period, temperature, and pH sufficient to convert at least a majority of the glucone isoflavones in the concentrate to aglucone isoflavones, and thereby produce an aglucone isoflavone enriched protein concentrate. The present invention also provides methods for producing such concentrates wherein supplemental beta-glucosidase is added to the wash or concentrate. The resulting aglucone enriched concentrate can then be separated and dewatered. In addition, the present invention provides methods of recovering, in relatively high proportions, isoflavones in protein concentrates, from vegetable protein materials.

DESCRIPTION OF THE PREFERRED EMBODIMENTS

Although the present invention will be described with respect to soybean products and although the process is particularly suited for the production of aglucone isoflavone enriched concentrated soybean materials, nevertheless the process is generally applicable to the production of an aglucone isoflavone enriched concentrate from a variety of vegetable protein sources which contain isoflavones. An example of a suitable vegetable protein material is a soy material, a soybean material, or a vegetable protein material comprising soybeans. The term "soybean material" as used herein refers to soybeans or any soybean derivative.

The starting material in accordance with the preferred embodiment concentrate is soybean flakes, from which the oil has been removed by solvent extraction. Typically, a soy protein concentrate is produced from soybean flakes by washing the flakes with an aqueous solvent having a pH at about the isoelectric point of the protein, which in the case of soy protein is about 4.4 to 4.6. An edible acid is typically added to the water to provide an isoelectric wash for the soy protein material. The isoelectric wash removes a large mount of water soluble carbohydrates and other components, but removes little of the protein to thereby provide a protein concentrate, which will typically have a protein content on a dry basis of about 60–75% by weight. The glucone isoflavones contained in the vegetable protein or soy material are removed by isoelectric washing. But because of the relatively low pH, the mounts removed are less than in higher pH extractions. Therefore, it is preferred for the purposes of the preferred embodiment and insofar as maximizing recovery of the isoflavones that isoelectric washing be limited to a single step or at most one additional wash be carried out, also at the isoelectric point. It is also preferred that the weight ratio of aqueous solvent used to wash the protein material relative to the mount of protein material is about 5:1 to about 10:1.

The resulting concentrate is suspended in water at a solids level of about 10 to about 15% by weight and then reacted with one or more beta-glucosidase enzymes to convert at least a majority and preferably substantially all the glucone isoflavone material contained in the concentrate to aglucone isoflavones. The optimum pH range for the beta-glucosidase enzyme will vary depending on the specific beta-glucosidase enzyme used, but typically will vary between about 4 and about 8. The pH of the extract is typically adjusted to about the pH range at which the specific enzyme is most active prior to reaction with the enzyme. The pH is typically adjusted by the addition of an edible acid, such as acetic, sulfuric, phosphoric, hydrochloric, or any other suitable reagent.

The beta-glucosidase enzyme may be naturally present in the soybean material or present from microbial growth, referred to herein as "residual" enzyme, or may be added to the concentrate. Added enzyme is referred to herein as "supplemental enzyme". Generally, if the concentration of residual enzyme in the concentrate is insufficient to convert a majority, and preferably substantially all, the isoflavones in glucone form to aglucone form, then supplemental enzyme should be added. The amount of enzyme sufficient to perform the conversion of isoflavones varies upon a multitude of factors, including the type of enzymes present, distribution of enzyme concentrations, pH of the system, and activities of enzymes present. Once sufficient concentrations of enzymes are present, either via residual enzymes, supplemental enzymes, or both, the concentrate is reacted with the beta-glucosidase enzymes for a time period, temperature, and pH sufficient to convert at least a majority and preferably substantially all the glucone isoflavones contained in the concentrate to the aglucone form.

Preferred supplemental beta-glucosidase enzymes include Biopectinase 100L and 300L, Biopectinase OK 70L, Lactase F, and Lactozyme. Lactase F is available from Amano International Enzyme Co., Inc., P.O. Box 1000, Troy, Va. 22974, which has an optimum pH range of about 4–6, and Lactozyme is available from Novo Industries, Enzyme Division, Novo Alle, DK-2880 Bagsvaerd, Denmark, which has an optimum pH range of about 7. Biopectinase 100L, Biopectinase 300L, and Biopectinase OK 70L are available from Quest International, Sarasota, Fla. Supplemental enzymes are added in amounts sufficient to convert at least a majority and preferably substantially all the glucone isoflavones to aglucones. In instances where it is necessary to add supplemental enzymes, the mount of enzyme added is about 0.5% to about 5% by weight of the protein concentrate on a dry basis.

Another class of enzymes suitable for administration as supplemental enzymes are esterase enzymes. These enzymes are believed to be well suited to the preferred embodiment processes described herein as they convert the acetate and malonate conjugates to glucone isoflavones by removing the acetate and malonate groups from the isoflavone conjugates. In the most preferred embodiment, both types of enzymes, beta-glucosidase and esterase enzymes are utilized.

The processes of the preferred embodiment are preferably one-step processes and achieve very high degrees of conversion of isoflavones (from glucone form to aglucone form), in relatively short time periods, and with relative ease and economy. The term "one-step" reaction process as used herein refers to a reaction process in which certain process parameter values are generally maintained over the course of the reaction process. These process parameters include pH and temperature.

The very high degrees of conversion are such that at least a majority, and preferably, substantially all the isoflavones in glucone form present in the concentrate are convened to aglucone form. The term "a majority" refers to extent of conversion of glucone isoflavones to aglucone isoflavones of at least about 50%. The term "substantially all" refers to extent of conversion of glucone isoflavones to aglucone isoflavones of at least about 80%, and most preferably at least about 90%.

Although not wishing to be bound to any particular theory, it is believed that the surprisingly and unexpectedly high degrees of conversion of the processes described here in result from a combination of process parameters utilized during the one-step reaction process. It is preferred that pH of the reaction system be maintained, or approximately so, at a value of about 4 to about 8, and most preferably at a value at which the enzyme(s) are most active prior to reaction with the isoflavone conjugate(s) during the one-step reaction process. It is preferred that the temperature of the reaction system be maintained, or approximately so, at a temperature of from about 40° C. to about 60° C., and most preferably at a temperature of about 60° C. during the one-step reaction process. Generally, the time periods necessary to achieve conversion of substantially all glucone isoflavones to aglucones via the one-step processes described herein are from about 2 hours to about 24 hours.

An alternative procedure for providing an aglucone enriched concentrate is to combine isoelectric washing and reaction with the beta-glucosidase enzymes into a single step, wherein the soy starting material is suspended in the isoelectric wash and one or more beta-glucosidase enzymes having an optimum pH at about the isoelectric point such as Lactase F described above is added directly to the slurry. Reaction is then carried out under the previously described general conditions to convert at least a majority and preferably substantially all the glucone isoflavones to aglucones. This represents a preferred and simplified process without first washing the material at the isoelectric point to remove soluble carbohydrates and thereby avoid any possible loss of the isoflavones by washing.

The protein concentrate can then be dewatered by conventional procedures including centrifugation and drying techniques to provide a concentrate having a genistein level on a dry basis of about 1.0 to about 2.0 mg/gram and a daidzein level on a dry basis of about 0.7 to about 1.5 mg/gram.

The present invention also provides methods of recovering isoflavones in a protein concentrate, in very high proportions, from a vegetable protein material such as a soybean material. The recovery levels obtainable by the processes described herein are typically at least 50%, preferably 65%, and most preferably 80%, based upon the total of all forms of the particular isoflavone in the starting vegetable protein material. Although not wishing to be bound to any particular theory, it is believed that the high recoveries stem from the conversion reactions described herein coupled with the various processing operations also described. By converting glucone isoflavone conjugates, which are relatively soluble, to less soluble aglucone forms, at a particular stage of processing, it is possible to recover in the resulting product, a high percentage of the isoflavones from the feed material.

The following examples describe specific but non-limiting embodiments of the present invention.

EXPERIMENTAL

A mixture of 15 grams soybean meal and 150 grams of water was adjusted to a pH of 7. 1.5 grams of Biopectinase 100L was added to the mixture. The mixture was incubated at 60° C. for two hours at which time the pH was adjusted to 4.5. An additional 1 gram of Biopectinase 100L was added and the resulting mixture was incubated for two hours. After incubation, the resulting aglucone isoflavone enriched protein/fiber concentrate was recovered. Recovery of isoflavones in the protein/fiber concentrate is reported in Table 1 set forth below.

Lactase F, was added. The slurry was allowed to react for 16 hours at 50° C. to ensure complete conversion of the glucone isoflavones to the aglucone form. The protein concentrate was separated from the aqueous solvent by centrifugation to form an aglucone enriched concentrate. Further washing of the concentrate was avoided. The amount of genistein recovered in the isolate was 82% of the total of all forms of genistin and genistein in the starting soybean material (defatted soy flour). Similarly, the amount of daidzein recovered in the isolate was 64%.

The following is a description of a method for quantifying isoflavones in soy products. The isoflavones are extracted from soy products by mixing 0.75 gram of sample (spray dried or freely ground powder) with 50 ml of 80/20 methanol/water solvent. The mixture is shaken for 2 hours at room temperature with an orbital shaker. After 2 hours, the remaining undissolved materials are removed by fitration through Whatman No. 42 filter paper. Five ml of the filtrate are diluted with 4 ml of water and 1 ml of methanol.

The extracted isoflavones are separated by HPLC (High Performance Liquid Chromatography) using a Beckman C18 reverse phase column. The isoflavones are injected on to the column and eluted with a solvent gradient starting with 88% methanol, 10% water, and 2% glacial acetic acid and ending with 98% methanol and 2% glacial acetic acid. At a flow rate of 0.4 ml/min, all the isoflavones—genistin, 6"-0-Acetylgenistin, 6"-0-Malonylgenistin, genistein, daidzin, 6"-0-Acetyldaidzin, 6"-0-Malonyldaidzin, daidzin, glycitin and its derivatives and glycitein—are clearly resolved. Peak detection is by UV absorbance at 262 mm. Identification of the peaks was by mass spectrometer.

TABLE 1

| SAMPLE | GENISTIN % | 6"-OMAL-GENISTIN % | 6"-OAC-GENISTIN % | GENISTEIN % | DAIDZIN % | 6"-OMAL-DAIDZIN % |
|---|---|---|---|---|---|---|
| One-Step Conversion | | | | | | |
| Starting material | 48 | 49 | 0 | 3 | 47 | 47 |
| Protein/Fiber Conc. | 8 | 27 | 0 | 66 | 7 | 23 |

| SAMPLE | 6"-OAC-DAIDZIN % | DAIDZEIN % | GLYCITIN % | 6"-OMAL-GLYCITIN % | GLYCITEIN % |
|---|---|---|---|---|---|
| One-Step Conversion | | | | | |
| Starting material | 1 | .4 | 43 | 41 | 16 |
| Protein/Fiber Conc. | 0 | 70 | 50 | 15 | 35 |

These data indicate the degree of conversion attainable by a combination of residual enzyme(s) and supplemental enzyme. Significant conversion of isoflavone conjugates to aglucones occurred, particularly for genistein and daidzein. The concentration of each type of isoflavone described herein is based upon the total of all forms of that isoflavone type.

In another series of experiments, the percent recovery of genistein and daidzein in a protein concentrate derived from soybeans was investigated. The percent recovery was found by determining the amount of genistein (or daidzein) in the isolate, and expressing that amount as a percentage based upon the total amount of all forms of genistein (or daidzein) in the soybean starting material. 100 g of defatted soy flour was added to 1600 g of water which had been adjusted to a pH of 4.5 by the addition of hydrochloric acid. The slurry was heated to 50° C., and 2% by dry weight of the curd of an enzyme having beta-glucosidase activity, specifically Quantification is achieved by using pure standards (genistin, genistein, daidzin and daidzein) purchased from Indofine Chemical Company, Sommerville, N.J. Response factors (Integrated area/concentration) are calculated for each of the above compounds and are used to quantitate unknown samples. For the conjugated forms for which no pure standards are available, response factors are assumed to be that of the parent molecule but corrected for molecular weight difference. The response factor for glycitin is assumed to be that for genistin corrected for molecular weight difference.

This method provides the quantities of each individual isoflavone. For convenience, total genistein, total daidzein and total glycitein can be calculated from the above data and represent the aggregate weight of these compounds if all the conjugated forms are converted to their respective unconjugated forms. These totals can also be measured directly by a method using acid hydrolysis to convert the conjugated forms.

Of course, it is understood that the foregoing are merely preferred embodiments of the invention and that various changes and alterations can be made without departing from the spirit and broader aspects thereof as set forth in the appended claims, which are to be interpreted in accordance with the principals of patent law including the Doctrine of Equivalents.

The embodiments of the invention in which an exclusive property or privilege is claimed are defined as follows:

1. A process for producing an aglucone isoflavone enriched protein concentrate from a vegetable protein material comprising:
   (a) washing a vegetable protein material comprising glueone isoflavones with an aqueous solvent having a pH at about the isoelectric point of said vegetable protein material to produce a vegetable protein concentrate comprising glucone isoflavones; and
   (b) reacting said glucone isoflavones with a sufficient amount of enzyme which is at least one of beta-glucosidase enzyme and esterase enzyme for a time period, temperature, and pH sufficient to convert at least a majority of said glucone isoflavones in said concentrate to aglucone isoflavones, and thereby produce an aglucone isoflavone enriched protein concentrate.

2. The process as set forth in claim 1 wherein said time period is from about 2 hours to about 24 hours.

3. The process as set forth in claim 2 whereto said time period is about 24 hours.

4. The process as set forth in claim 1 wherein said temperature is about 40° C. to about 60° C.

5. The process as set forth in claim 4 wherein said temperature is about 60° C.

6. The process as set forth in claim 1 wherein the pH of the reacting step is from about 4 to about 8.

7. The process as set forth in claim 6 wherein the pH of the reacting step is about 4.5.

8. The process as set forth in claim 1 wherein said time period is about 24 hours, said temperature is about 60° C., and the pH of the reacting step is about 4.5.

9. The process as set forth in claim 1 wherein the steps of washing said vegetable protein material and reacting said glucone isoflavones with said beta glucosidase enzyme is performed in one operation.

10. The aglucone isoflavone enriched protein concentrate produced by the method of claim 1.

11. The process as set forth in claim 1 wherein said aglucone isoflavone enriched protein concentrate is made from soybeans.

12. The process as set forth in claim 1 wherein said vegetable protein material comprises a soybean material.

13. The process as set forth in claim 1 wherein substantially all glucone isoflavones are converted to aglucone isoflavones.

14. A process for producing an aglucone isoflavone enriched protein concentrate from a vegetable protein material comprising:
   (a) washing a vegetable protein material comprising glucone isoflavones and sufficient residual enzyme which is at least one of beta-glucosidase enzyme or esterase enzyme, with an aqueous solvent having a pH at about the isoelectric point of said vegetable protein material to produce a vegetable protein concentrate comprising glucone isoflavones; and
   (b) reacting said glucone isoflavones with said residual enzyme for a time period, temperature, and pH sufficient to convert at least a majority of said glucone isoflavones in said concentrate to aglucone isoflavones, and thereby produce an aglucone isoflavone enriched protein concentrate.

15. The process as set forth in claim 14 wherein said time period is from about 2 hours to about 24 hours.

16. The process as set forth in claim 15 wherein said time period is about 24 hours.

17. The process as set forth in claim 14 wherein said temperature is about 40° C. to about 60° C.

18. The process as set forth in claim 17 wherein said temperature is about 60° C.

19. The process as set forth in claim 14 wherein the pH of the reacting step is from about 4 to about 8.

20. The process as set forth in claim 19 wherein the pH of the reacting step is about 4.5.

21. The process as set forth in claim 14 wherein said time period is about 24 hours, temperature is about 60° C., and the pH of the reacting step is about 4.5.

22. The process as set forth in claim 14 wherein the steps of washing said vegetable protein material and reacting said glucone isoflavones with said beta glucosidase enzyme are performed in one operation.

23. The aglucone isoflavone enriched protein concentrate produced by the method of claim 14.

24. The process as set forth in claim 14 wherein said concentrate is made from soybeans.

25. The process as set forth in claim 14 wherein said vegetable protein material comprises a soybean material.

26. The process as set forth in claim 14 wherein substantially all glucone isoflavones are converted to aglucone isoflavones.

27. A process for producing an aglucone isoflavone enriched protein concentrate from a vegetable protein material comprising:
   (a) washing a vegetable protein material comprising glucone isoflavones with an aqueous solvent having a pH at about the isoelectric point of said vegetable protein material to produce a vegetable protein concentrate comprising glucone isoflavones;
   (b) adding supplemental enzyme which is at least one of beta-glucosidase enzyme and esterase enzyme to said concentrate so that the total concentration of enzyme in said concentrate is sufficient to convert at least a majority of said glucone isoflavones in said concentrate to aglucone isoflavones; and
   (c) reacting said glucone isoflavones with said enzyme for a time period, temperature, and pH sufficient to convert at least a majority of said glucone isoflavones in said concentrate to aglucone isoflavones, and thereby produce an aglucone isoflavone enriched concentrate.

28. The process as set forth in claim 27 wherein said time period is from about 2 hours to about 24 hours.

29. The process as set forth in claim 28 wherein said time period is about 24 hours.

30. The process as set forth in claim 27 wherein said temperature is about 40° C. to about 60° C.

31. The process as set forth in claim 30 wherein said temperature is about 60° C.

32. The process as set forth in claim 27 wherein the pH of the reacting step is from about 4 to about 8.

33. The process as set forth in claim 32 wherein the pH of the reacting step is about 4.5.

34. The process as set forth in claim 27 wherein said time period is about 24 hours, said temperature is about 60° C., and the pH of the reacting step is about 4.5.

35. The process as set forth in claim 27 wherein the steps of washing said vegetable protein material and reacting said glucone isoflavones with said beta glucosidase enzyme are performed in one operation.

36. The aglucone isoflavone enriched concentrate produced by the method of claim 27.

37. The process as set forth in claim 27 wherein said concentrate is made from soybeans.

38. The process as set forth in claim 27 wherein said vegetable protein material comprise a soybean material.

39. The process as set forth in claim 27 wherein substantially all glucone isoflavones are converted to aglucone isoflavones.

40. An aglucone isoflavone enriched protein concentrate having on a dry basis a genistein content of about 1.0 to about 2.0 mg/gram and a daidzein content of about 0.7 to about 1.5 mg/gram.

41. The process as set forth in claim 1 wherein the pH of the reacting step is at a value at which said enzyme is most active prior to reaction with said isoflavones.

42. The process as set forth in claim 14 wherein the pH of the reacting step is at a value at which said residual enzyme is most active prior to reaction with said isoflavones.

43. The process as set forth in claim 27 wherein the pH of the reacting step is at a value at which said supplemental enzyme is most active prior to reaction with said isoflavones.

44. A process for recovering in a protein concentrate, at least 50% of an isoflavone in a vegetable protein material comprising:

(a) washing a vegetable protein material comprising isoflavones with an aqueous solvent having a pH at about the isoelectric point of said vegetable protein material to produce a vegetable protein concentrate comprising said isoflavones;

(b) reacting said isoflavones with a sufficient amount of an enzyme for a time period, temperature, and pH sufficient to convert at least a majority of said isoflavones in said concentrate to less soluble isoflavones, and thereby produce an isoflavone enriched protein concentrate containing at least 50% of the isoflavones in said vegetable protein material.

45. The process as set forth in claim 44 wherein said concentrate contains at least 65% of the isoflavones in said vegetable protein material.

46. The process as set forth in claim 44 wherein said concentrate contains at least 80% of the isoflavones in said vegetable protein material.

47. The concentrate produced by the method of claim 44.

48. The concentrate produced by the method of claim 45.

49. The concentrate produced by the method of claim 46.

50. The process as set forth in claim 44 wherein said vegetable protein material comprises a soybean material.

51. The process as set forth in claim 44 wherein said enzyme is selected from the group consisting of beta-glucosidase enzyme and esterase enzyme.

* * * * *